(12) United States Patent
Swayze et al.

(10) Patent No.: US 7,758,512 B2
(45) Date of Patent: Jul. 20, 2010

(54) ELECTROACTIVE POLYMER-BASED LUMEN TRAVERSING DEVICE

(75) Inventors: Jeffrey Swayze, Hamilton, OH (US); Mark Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1074 days.

(21) Appl. No.: 11/161,262

(22) Filed: Jul. 28, 2005

(65) Prior Publication Data

US 2007/0038237 A1 Feb. 15, 2007

(51) Int. Cl.
*A61M 25/00* (2006.01)

(52) U.S. Cl. ..................................... 600/528

(58) Field of Classification Search ................ 604/528, 604/533; 600/146, 114
See application file for complete search history.

(56) References Cited

U.S. PATENT DOCUMENTS

| | | | |
|---|---|---|---|
| 5,389,222 A | | 2/1995 | Shahinpoor |
| 5,398,670 A | * | 3/1995 | Ortiz et al. ............ 600/114 |
| 6,249,076 B1 | | 6/2001 | Madden et al. |
| 6,514,237 B1 | * | 2/2003 | Maseda .................. 604/533 |
| 6,667,825 B2 | | 12/2003 | Lu et al. |
| 6,679,836 B2 | * | 1/2004 | Couvillon, Jr. ......... 600/146 |
| 7,049,732 B2 | * | 5/2006 | Pei et al. ................ 310/365 |
| 2003/0229332 A1 | | 12/2003 | Intoccia |
| 2003/0236531 A1 | | 12/2003 | Couvillon |
| 2004/0143160 A1 | | 7/2004 | Couvillon |
| 2004/0167546 A1 | | 8/2004 | Saadat et al. |
| 2005/0085693 A1 | | 4/2005 | Belson et al. |
| 2005/0113892 A1 | | 5/2005 | Sproul |

FOREIGN PATENT DOCUMENTS

WO 03/028547 A2 4/2003

OTHER PUBLICATIONS

Mexican Office Action for Application No. PA/A/2006/008649, dated May 13, 2009. (6 pages).
European Search Report for 06253937 dated Dec. 18, 2006. (9 pages).
Slatkin A B et al., "The Development of a Robotic Endoscope" Int'l Conf. on Intelligentrobots and Systems: Human Robot Interaction and Cooperative Robots. Pittsburgh, PA, Aug. 5-9, 1995, Proceedings of the ieee/rsj, vol. vol. 2, Aug. 5, 1995, xp000697561, pp. 162-171.

* cited by examiner

*Primary Examiner*—Nicholas D Lucchesi
*Assistant Examiner*—Diva Ranade
(74) *Attorney, Agent, or Firm*—Dean Garner

(57) ABSTRACT

Methods and devices are provided for traversing a lumen of a tubular body part, such as the large or small intestine, the colon, the bladder, the stomach, etc. In an exemplary embodiment, the methods and devices utilize electroactive polymers that are selectively actuated to move a device through a lumen.

17 Claims, 6 Drawing Sheets

ELECTROACTIVE POLYMER-BASED LUMEN TRAVERSING DEVICE

FIELD OF THE INVENTION

The present invention relates broadly to surgical devices, and in particular to methods and devices for traversing a lumen using electroactive polymers.

BACKGROUND OF THE INVENTION

Many different medical devices are passed through a lumen of a tubular body part for diagnostic and/or delivery purposes. An endoscope, for example, is an instrument that is used for visually examining the interior of a bodily canal or a hollow organ, such as the colon, bladder, stomach, or intestines. During a procedure involving use of an endoscope, the instrument must be carefully navigated through the tubular body part in order to avoid perforating the intraluminal wall of the body part.

Many techniques can be used to move an endoscope through a lumen. Most endoscopes are forced through the tubular body part and a mechanical articulation mechanism is used to manipulate the endoscope around turns. More recently, endoscopes have been developed that employ distal, intermediate, and proximal inflatable cuffs that are selectively inflated and deflated to effect migration of the distal end of the instrument through the lumen of a tubular body part. The distal cuff, which is secured to a sheath that surrounds the fibers used to obtain and transmit an image, is expanded radially while the proximal and intermediate cuffs are secured to the distal cuff, respectively, and are axially slidable on the sheath. The proximal cuff is expanded radially while the intermediate cuff is expand axially. While the use of expandable cuffs can be an effective propulsion mechanism to push and pull the device through a tubular body part, difficulty can be encountered when navigating sharp turns in the tubular body part. The inflatable cuffs do not provide for angular manipulation of the device.

Accordingly, there is a need for improved methods and devices for traversing a tubular body part.

BRIEF SUMMARY OF THE INVENTION

The present invention generally provides methods and devices for traversing a lumen of a tubular body part. In one exemplary embodiment, a lumen traversing medical device is provided having a flexible elongate member with proximal and distal actuators coupled to proximal and distal portions thereof and adapted to expand radially to engage an inner wall of a lumen upon application of energy thereto, and an intermediate actuator coupled thereto and positioned between the proximal and distal actuators. The intermediate actuator is adapted to change a length of the flexible elongate member upon application of energy thereto. In one embodiment, the intermediate actuator can be adapted to expand axially and contract radially to increase a length of the flexible elongate member. Alternatively, the intermediate actuator can be adapted to expand radially and contract axially to decrease a length of the flexible elongate member. In use, each actuator can include a return electrode and an active energy-delivering electrode coupled thereto, and the actuators can be sequentially actuated with energy to move the device through a lumen. The flexible elongate member can be incorporated into a medical device, or it can contain a medical device therein for moving the device through a lumen.

While the actuators can be coupled to the flexible elongate member in a variety of configurations, in one embodiment the proximal and distal actuators can be disposed around proximal and distal portions of the flexible elongate member, and the intermediate actuator can be disposed between the proximal and distal actuators and it can extend along at least a portion of a length of the flexible elongate member. The intermediate actuator can be, for example, a plurality of elongate bands extending along at least a portion of a length of the flexible elongate member. In one exemplary embodiment, the elongate bands can be spaced substantially equidistant from one another around a circumference of the flexible elongate member.

The actuators can also have a variety of configurations. For example, the proximal, distal, and intermediate actuators can each include a flexible conductive outer shell having an electroactive polymer and an ionic fluid disposed therein. Alternatively, each actuator can include at least one electroactive polymer composite having at least one flexible conductive layer, an electroactive polymer layer, and an ionic gel layer.

The medical device can also include a variety of other components, depending on the intended use. For example, in one exemplary embodiment the medical device can be an endoscope. The distal portion of the flexible elongate member can thus include an imaging mechanism disposed therein for viewing a lumen.

In another exemplary embodiment, a medical device for traversing a lumen of a tubular body part is provided and includes a flexible elongate member having a plurality of actuators coupled thereto. At least two of the actuators can be lumen-engaging actuators that are adapted to expand radially upon delivery of energy thereto to engage a lumen of a tubular body part, and at least another one of the actuators can be a lumen-traversing actuator that is adapted to change a length of at least a portion of the flexible elongate member upon application of energy thereto to move the flexible elongate member a distance through a lumen. In certain exemplary embodiment, the flexible elongate member includes a plurality of lumen-engaging actuators spaced a distance apart from one another, and a plurality of lumen-traversing actuators extending between the lumen-engaging actuators. In use, the actuators are preferably adapted to be sequentially actuated with energy to move the device through a lumen.

In other aspects, a method for traversing a lumen of a tubular body part is provided and includes positioning an elongate tubular member in a lumen of a tubular body part, and sequentially electrically actuating various portions of the elongate tubular member to cause the portions to engage the lumen and to change a length of the elongate tubular member to move the elongate tubular member a distance through the lumen of the tubular body part. The various portions of the elongate tubular member can be, for example, a plurality of actuating members coupled to the elongate tubular member. For example, at least two lumen-engaging actuating members can be disposed around the elongate tubular member to expand radially to engage the lumen when electrically actuated, and at least one lumen-traversing actuating member can extend axially along at least a portion of a length of the elongate tubular member to change a length of the elongate tubular member to move the elongate tubular member a distance through the lumen.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
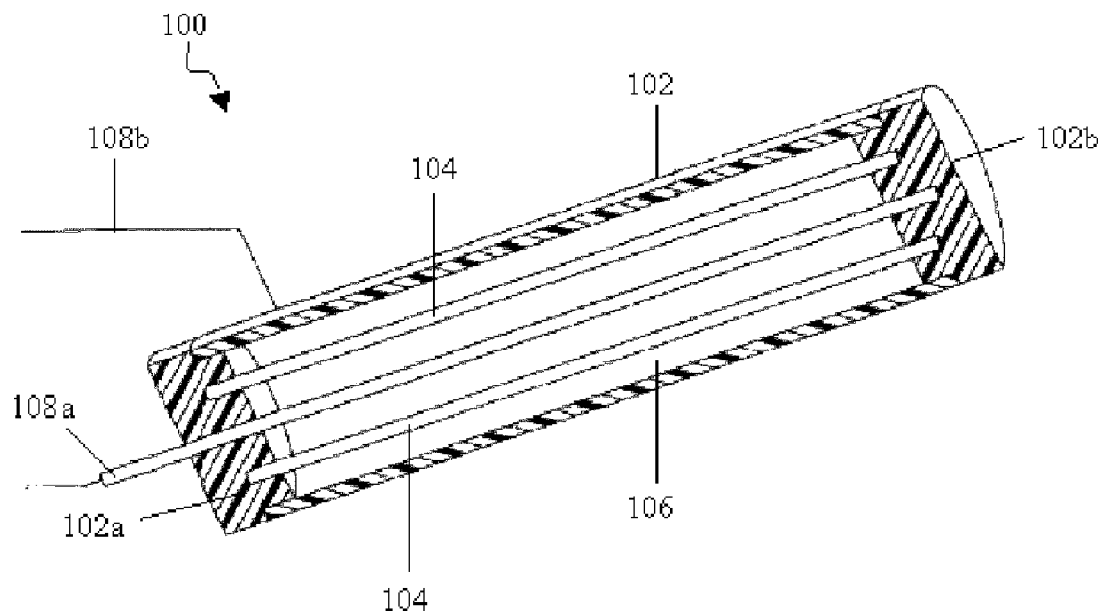
FIG. 1A is a cross-sectional view of a prior art fiber bundle type EAP actuator.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for traversing a lumen of a tubular body part, such as the large or small intestine, the colon, the bladder, the stomach, etc. In an exemplary embodiment, the methods and devices utilize electroactive polymers that are selectively actuated to move a device through a lumen. A person skilled in the art will appreciate that methods and devices disclosed herein can have a variety of configurations, and they can be adapted for use in a variety of medical procedures. For example, the methods and devices can be used for diagnostic purposes, such as for examining the intraluminal wall of a tubular body part, or as a delivery means for delivering air, water, light, energy, medications, radiopaque agents, etc.

As indicated above, in an exemplary embodiment electroactive polymers can be used to move a device through a lumen of a tubular body part. Electroactive polymers (EAPs), also referred to as artificial muscles, are materials that exhibit piezoelectric, pyroelectric, or electrostrictive properties in response to electrical or mechanical fields. In particular, EAPs are a set of conductive doped polymers that change shape when an electrical voltage is applied. The conductive polymer can be paired with some form of ionic fluid or gel using electrodes. Upon application of a voltage potential to the electrodes, a flow of ions from the fluid/gel into or out of the conductive polymer can induce a shape change of the polymer. Typically, a voltage potential in the range of about 1V to 4 kV can be applied depending on the particular polymer and ionic fluid or gel used. It is important to note that EAPs do not change volume when energized, rather they merely expand in one direction and contract in a transverse direction.

One of the main advantages of EAPs is the possibility to electrically control and fine-tune their behavior and properties. EAPs can be deformed repetitively by applying external voltage across the EAP, and they can quickly recover their original configuration upon reversing the polarity of the applied voltage. Specific polymers can be selected to create different kinds of moving structures, including expanding, linear moving, and bending structures. The EAPs can also be paired to mechanical mechanisms, such as springs or flexible plates, to change the effect of the EAP on the mechanical mechanism when voltage is applied to the EAP. The amount of voltage delivered to the EAP can also correspond to the amount of movement or change in dimension that occurs, and thus energy delivery can be controlled to effect a desired amount of change.

There are two basic types of EAPs and multiple configurations for each type. The first type is a fiber bundle that can consist of numerous fibers bundled together to work in cooperation. The fibers typically have a size of about 30-50 microns. These fibers may be woven into the bundle much like textiles and they are often referred to as EAP yarn. In use, the mechanical configuration of the EAP determines the EAP actuator and its capabilities for motion. For example, the EAP may be formed into long strands and wrapped around a single central electrode. A flexible exterior outer sheath will form the other electrode for the actuator as well as contain the ionic fluid necessary for the function of the device. When voltage is applied thereto, the EAP will swell causing the strands to contract or shorten. An example of a commercially available fiber EAP material is manufactured by Santa Fe Science and Technology and sold as PANION™ fiber and described in U.S. Pat. No. 6,667,825, which is hereby incorporated by reference in its entirety.

Figure 1B:
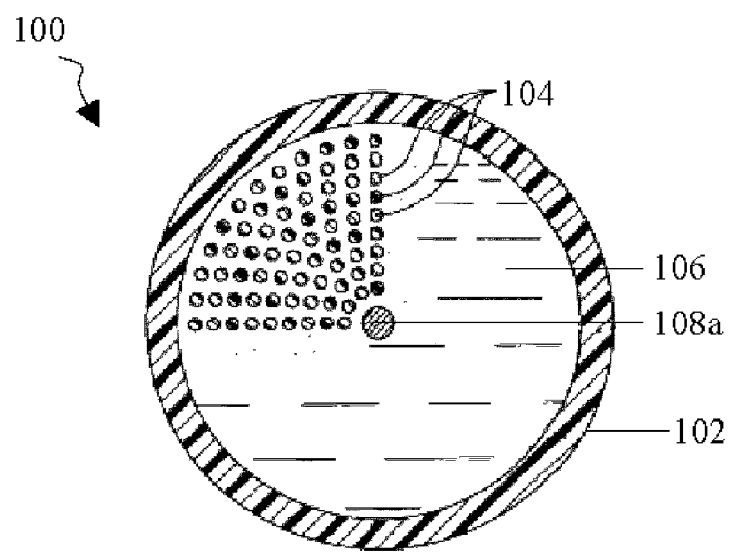
FIG. 1B is a radial cross-sectional view of the prior art actuator shown in FIG. 1A.

FIGS. 1A and 1B illustrate one exemplary embodiment of an EAP actuator 100 formed from a fiber bundle. As shown, the actuator 100 generally includes a flexible conductive outer sheath 102 that is in the form of an elongate cylindrical member having opposed insulative end caps 102a, 102b formed thereon. The conductive outer sheath 102 can, however, have a variety of other shapes and sizes depending on the intended use. As is further shown, the conductive outer sheath 102 is coupled to a return electrode 108a, and an energy delivering electrode 108b extends through one of the insulative end caps, e.g., end cap 102a, through the inner lumen of the conductive outer sheath 102, and into the opposed insulative end cap, e.g., end cap 102b. The energy delivering electrode 108b can be, for example, a platinum cathode wire. The conductive outer sheath 102 can also include an ionic fluid or gel 106 disposed therein for transferring energy from the energy delivering electrode 108b to the EAP fibers 104, which are disposed within the outer sheath 102. In particular, several EAP fibers 104 are arranged in parallel and extend between and into each end cap 102a, 120b. As noted above, the fibers 104 can be arranged in various orientations to provide a desired outcome, e.g., radial expansion or contraction, or bending movement. In use, energy can be delivered to the actuator 100 through the active energy delivery electrode 108b and the conductive outer sheath 102 (anode). The energy will cause the ions in the ionic fluid to enter into the EAP fibers 104, thereby causing the fibers 104 to expand in one direction, e.g., radially such that an outer diameter of each fiber 104 increases, and to contract in a transverse direction, e.g., axially such that a length of the fibers decreases. As a result, the end caps 102a, 120b will be pulled toward one another, thereby contracting and decreasing the length of the flexible outer sheath 102.

Another type of EAP is a laminate structure, which consists of one or more layers of an EAP, a layer of ionic gel or fluid disposed between each layer of EAP, and one or more flexible conductive plates attached to the structure, such as a positive plate electrode and a negative plate electrode. When a voltage is applied, the laminate structure expands in one direction and contracts in a transverse or perpendicular direction, thereby causing the flexible plate(s) coupled thereto to shorten or lengthen, or to bend or flex, depending on the configuration of the EAP relative to the flexible plate(s). An example of a commercially available laminate EAP material is manufactured by Artificial Muscle Inc, a division of SRI Laboratories. Plate EAP material, referred to as thin film EAP, is also available from EAMEX of Japan.

Figure 2A:
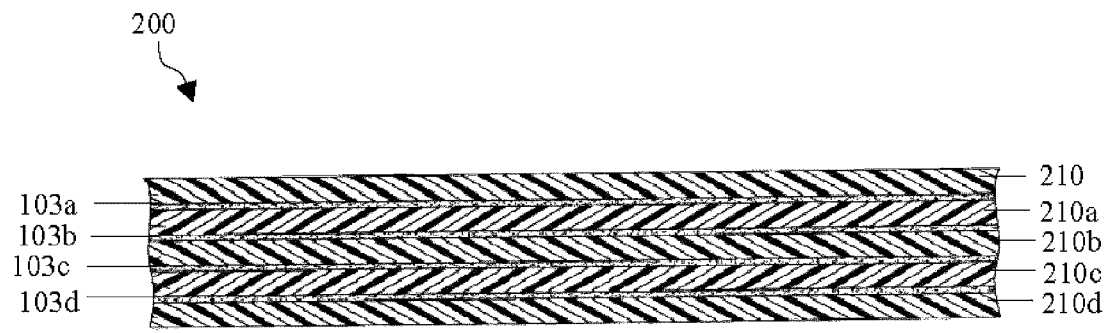
FIG. 2A is a cross-sectional view of a prior art laminate type EAP actuator having multiple EAP composite layers.
Figure 2B:
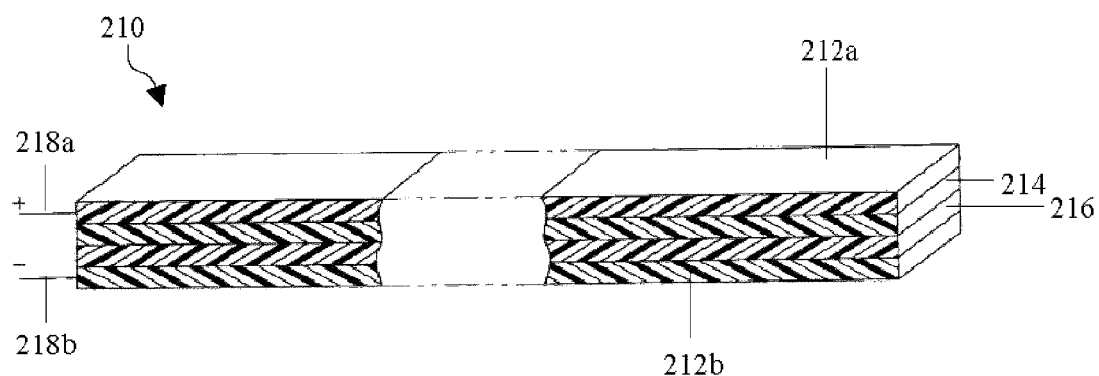
FIG. 2B is a perspective view of one of the composite layers of the prior art actuator shown in FIG. 2A.

FIGS. 2A and 2B illustrate an exemplary configuration of an EAP actuator 200 formed from a laminate. Referring first to FIG. 2A, the actuator 200 can include multiple layers, e.g., five layers 210, 210a, 210b, 210c, 210d are shown, of a laminate EAP composite that are affixed to one another by adhesive layers 103a, 103b, 103c, 103d disposed therebetween. One of the layers, i.e., layer 210, is shown in more detail in FIG. 2B, and as shown the layer 210 includes a first flexible conductive plate 212a, an EAP layer 214, an ionic gel layer 216, and a second flexible conductive plate 212b, all of which are attached to one another to form a laminate composite. The composite can also include an energy delivering electrode 218a and a return electrode 218b coupled to the flexible conductive plates 212a, 212b, as further shown in FIG. 2B. In use, energy can be delivered to the actuator 200 through the active energy delivering electrode 218a. The energy will cause the ions in the ionic gel layer 216 to enter into the EAP layer 214, thereby causing the layer 214 to expand in one direction and to contract in a transverse direction. As a result, the flexible plates 212a, 212b will be forced to flex or bend, or to otherwise change shape with the EAP layer 214.

Figure 3:
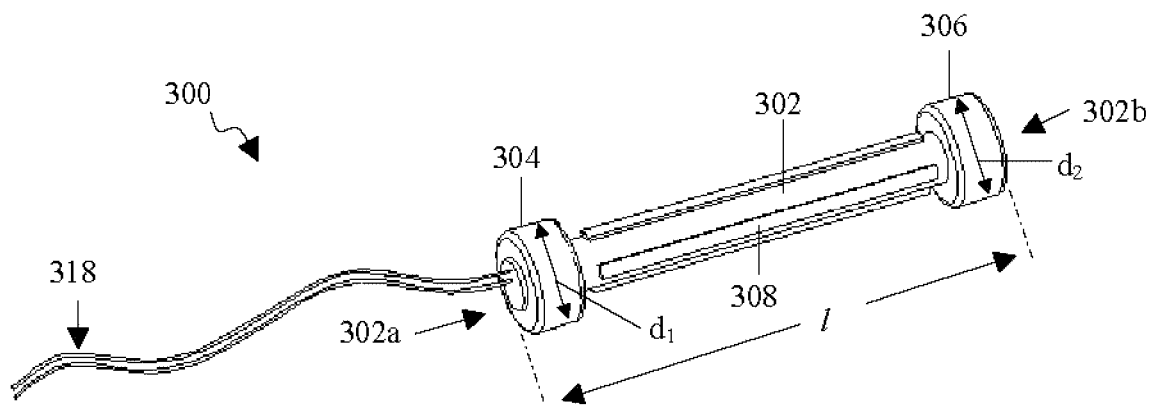
FIG. 3 is a perspective view of one exemplary embodiment of a lumen traversing device having multiple EAP actuators.
Figure 6:
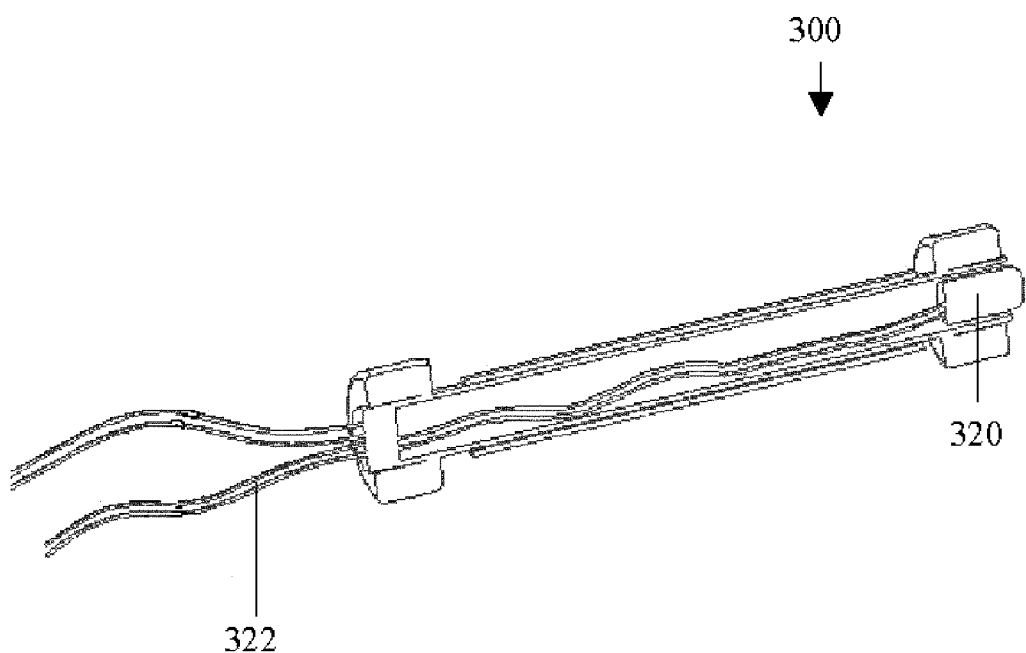
FIG. 6 is an axial cross-sectional view of the device shown in FIG. 3A.

As previously indicated, in an exemplary embodiment one or more EAP actuators can be incorporated into a medical device to move the device through a tubular body part. FIG. 3 illustrates one exemplary embodiment of such a device 300. As shown, the device 300 generally includes a flexible elongate member 302 having an inner lumen (not shown) extending therethrough between proximal and distal ends 302a, 302b thereof. While the illustrated elongate member 302 is substantially cylindrical, the shape, size, and configuration can vary depending on the intended use. For example, the flexible elongate member 302 can be adapted to contain various components therein. In one exemplary embodiment, as shown in FIG. 6, the device 300 can include an imaging mechanism 320 disposed within the inner lumen adjacent to the distal end 302b thereof for viewing the interior of a tubular body part or body organ. Imaging mechanisms are known in the art, and virtually any imaging mechanism can be used with the device 300. As is further shown in FIG. 6, signal leads 322 can be coupled to and extend from the imaging device 320 to deliver a signal to an external display. Alternatively, the device 300 can be adapted to contain or mate to one or more medical devices, such as an endoscope. In other embodiments, the inner lumen can be configured as a delivery vehicle for delivering fluids or other materials or devices to the body. A person skilled in the art will appreciate that the device 300 can be incorporated into or combined with a variety of medical devices. As will be discussed in more detail below, depending on the intended use and configuration of the device 300, the device 300 can be configured to push, pull, or move something through a lumen.

The flexible elongate member 302 can also be formed from a variety of materials to provide flexibility and/or elasticity thereto. In certain exemplary embodiments, the elongate member 302 is preferably formed from a biocompatible polymer, such as silicone or latex. Other suitable biocompatible elastomers include, by way of non-limiting example, synthetic polyisoprene, chloroprene, fluoroelastomer, nitrile, and fluorosilicone. A person skilled in the art will appreciate that the materials can be selected to obtain the desired mechanical properties.

As is further shown in FIG. 3, the flexible elongate member 302 also includes several EAP actuators 304, 306, 308 disposed thereon or coupled thereto. Each actuator 304, 306, 308 is coupled to an active energy delivering electrode and a return electrode. The electrodes 318 can extend through, be embedded within, or extend along an exterior of the flexible elongate member 302, and a variety of techniques known in the art can be used to coupled the electrodes to the actuators 304, 306, 308. In use, the actuators 304, 306, 308 can be configured to effect migration of the flexible elongate member 302 through a lumen upon selective delivery of energy thereto. For example, the actuators 304, 306, 308 can be sequentially electrically actuated in a predetermined order to engage the inner lumen of a tubular body part and to change (i.e., increase or decrease) a length of the flexible elongate member 302, thereby moving the elongate member 302 through the lumen, as will be explained in more detail below.

While various techniques can be used to achieve movement, and the EAP actuators 304, 306, 308 can have a variety of configurations, shapes, and sizes, in the exemplary embodiment shown in FIG. 3 the flexible elongate member 302 includes a proximal actuator 304, a distal actuator 306, and an intermediate actuator 308 disposed therebetween. The actuators 304, 306, 308 can be formed using either the laminate or fiber bundle type EAP, but in one exemplary embodiment the actuators 304, 306, 308 are formed from the laminate EAPs. Since each actuator 304, 306, 308 expands in one direction and contracts in a transverse direction, the orientation of the actuators 304, 306, 308 with respect to the flexible elongate member 302 can determine a direction of movement of each actuator 304, 306, 308. Also, differential expansion of one EAP actuator relative to another EAP actuator can determine a direction of the EAP. In an exemplary embodiment, the proximal and distal actuators 304, 306 are lumen-engaging actuators that are configured to expand radially to engage the inner lumen of a tubular body part, and the intermediate actuator 308 is a lumen-traversing actuator that it is configured to expand axially to increase the length of the flexible elongate member 302. To achieve this effect the proximal and distal actuators 304, 306 can be disposed radially around proximal and distal portions of the elongate member 302, and the intermediate actuator 308 can extend axially along a length of the elongate member 302 between the proximal and distal actuators 304, 306. While the intermediate actuator 308 extends between the proximal and distal actuators 304, 306, the intermediate actuator 308 preferably terminates adjacent to the proximal and distal actuators 304, 306 such that the actuators 304, 306, 308 are not in contact with one another and can therefore be individually electrically actuated. Alternatively, each actuator 304, 306, 308 can have a conductive polymer coating disposed therearound to allow the actuators to be in contact with one another without allowing energy transfer therebetween. Moreover, while the intermediate actuator 308 is described as being configured to expand axially to increase a length/of the elongate member 302, the intermediate actuator 308 could alternatively be configured to expand radially and contract axially to decrease the length/of the elongate member 302.

Where a laminate EAP composite is used to form the actuators 304, 306, 308, the laminate EAP composite can be shaped, e.g., rolled, to form the ring-like or circular proximal and distal actuators 304, 306, and one or more elongate plates or bands of a laminate EAP composite can be used to form the intermediate actuator 308. In an exemplary embodiment, as shown in FIG. 3, the intermediate actuator 308 can be formed from multiple actuators or bands of a laminate EAP composite. The bands can be positioned along various portions of the elongate member 302 to affect a desired movement, but in one exemplary embodiment they are preferably spaced substantially equidistant from one another around a circumference of the elongate member 302. Alternatively, the intermediate actuator 308 can be disposed around the entire circumference of the flexible elongate member 302.

Figure 4:
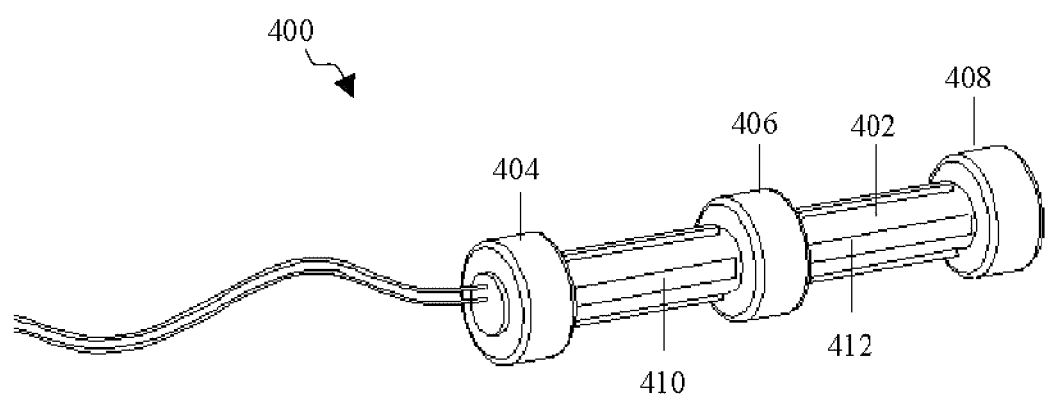
FIG. 4 is a perspective view of another exemplary embodiment of a lumen traversing device having multiple EAP actuators.

A person skilled in the art will appreciate that, while FIG. 3A illustrates a device 300 having only three actuators 304, 306, 308, the device 300 can include any number of actuators to facilitate movement of the device around turns and bends. By way of non-limiting example, FIG. 4 illustrates another embodiment of a device 400 having a flexible elongate member 402 with three lumen-engaging actuators 302, 304, 306, and two lumen-traversing actuators 308, 310 extending between the lumen-engaging actuators 302, 304, 306, respectively. The actuators can also have a variety of other configurations, shapes, and sizes to alter use of the device. For example, the lumen-traversing actuators can vary in axial length to vary the "stroke" of the device, and the lumen-engaging actuators could each be formed from multiple ring-shaped members to allow the actuator itself to bend around turns. The actuators can also be formed on the inside of a tubular member such that they are adapted to engage a structure, such as a guide wire, catheter, or other device, extending therethrough. A person skilled in the art will appreciate that a variety of configurations are possible to provide a device that is adapted to traverse through a lumen using electroactive polymers.

Referring back to FIG. 3, in use, when energy is delivered to the proximal and distal actuators 304, 306 through the electrodes 318, the actuators 304, 306 will expand radially and contract axially to cause a diameter $d_1$, $d_2$ of each actuator 304, 306 to increase. As a result, the proximal and distal actuators 304, 306 can engage the inner lumen of the tubular body part containing the device 300. To the contrary, since the intermediate actuator 308 extends in a direction transverse to a direction of the proximal and distal actuators 304, 306, the intermediate actuator 308 will expand axially and contract radially when energy is delivered thereto. The flexible elongate member 302 coupled to the intermediate actuator 308 will thus increase in length as the intermediate actuator 308 expands axially, thereby moving the proximal and distal ends 302a, 302b of the elongate member 302, as well as the proximal and distal actuators 304, 306 coupled thereto, away from another.

In certain exemplary embodiments, the lumen traversing device 300 can be used to examine and/or treat the gastrointestinal (GI) tract. Since the size of the device 300 can be relatively small, and since the leads extending from the device 300 are minimal, the device 300 can be inserted deeper than standard endoscopes and other intraluminal devices. For the upper GI, the device 300 can be inserted through a patient's mouth, and for the lower GI the device 300 can be inserted through the patient's anus. Regardless, the device 300 preferably has a size that allows the device 300 to engage the walls of and move through the GI tract. Typically, the maximum diameter of the GI tract is about 30 mm in the lower GI, and about 16 mm in the upper GI. Accordingly, in certain exemplary embodiments the proximal and distal actuators 304, 306 can have a diameter that ranges from about 16 mm in the unexpanded condition to about 33 mm in the expanded condition, and the intermediate actuator 308 can have a length that is about 4 inches in the unexpanded condition and about 5 inches in the expanded condition. The shape and size can, of course, vary depending on the intended use.

Figure 5A:
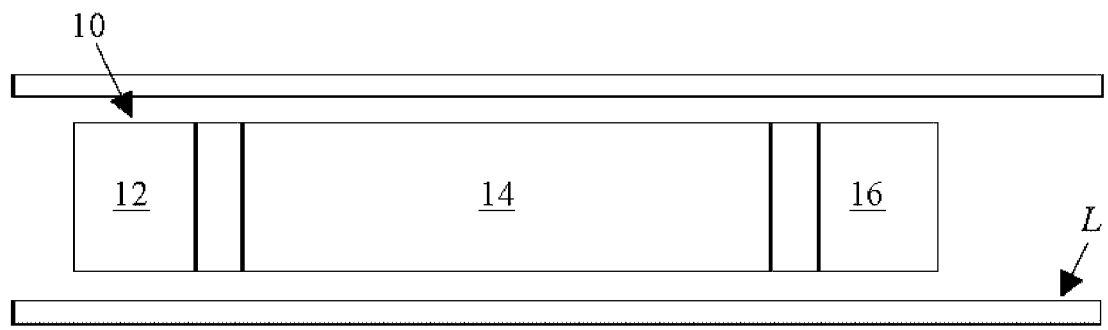
FIG. 5A is a schematic showing a lumen traversing device disposed within a lumen of a tubular body part.
Figure 5B:
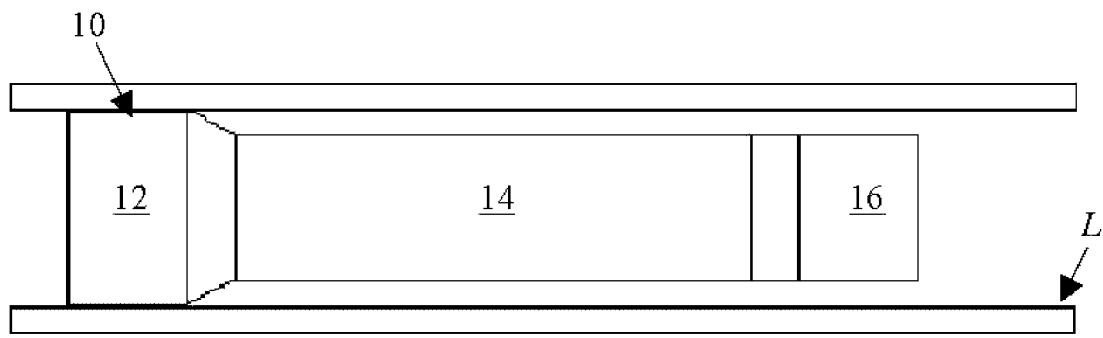
FIG. 5B is a schematic showing the lumen traversing device of FIG. 5A with a distal actuator electrically actuated to engage the lumen.
Figure 5C:
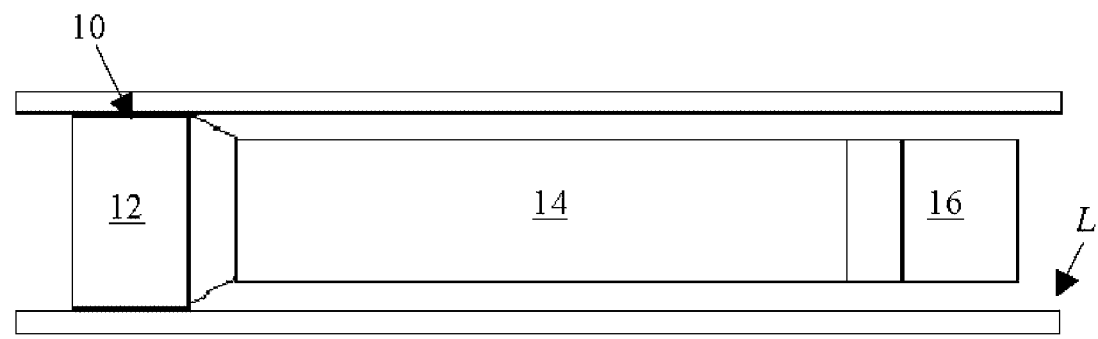
FIG. 5C is a schematic showing the lumen traversing device of FIG. 5B with an intermediate actuator electrically actuated to increase a length of the device.
Figure 5D:
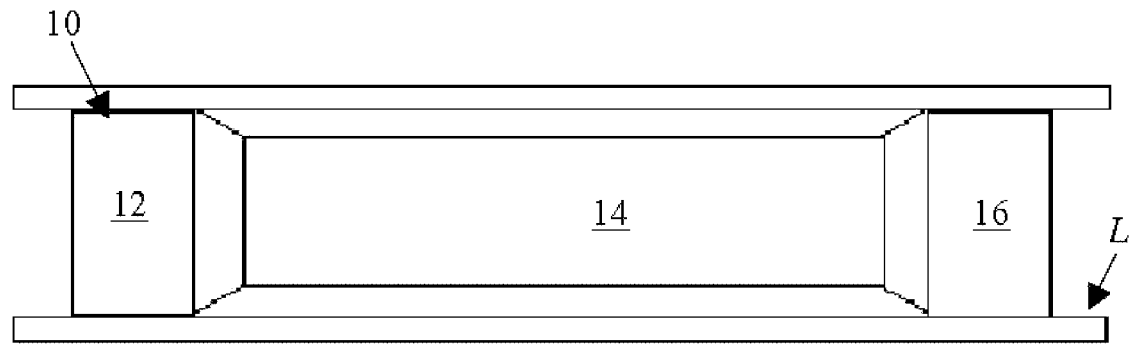
FIG. 5D is a schematic showing the lumen traversing device of FIG. 5C with a proximal actuator electrically actuated to engage the lumen.
Figure 5E:
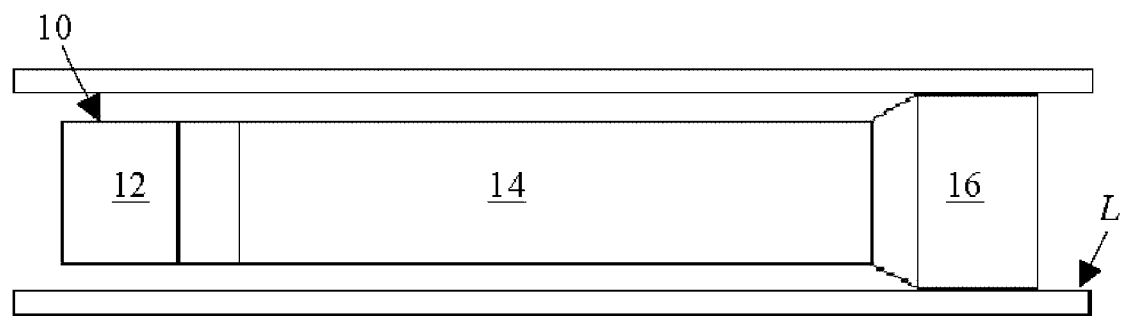
FIG. 5E is a schematic showing the lumen traversing device of FIG. 5A with the distal actuator electrically de-actuated to release the lumen.
Figure 5F:
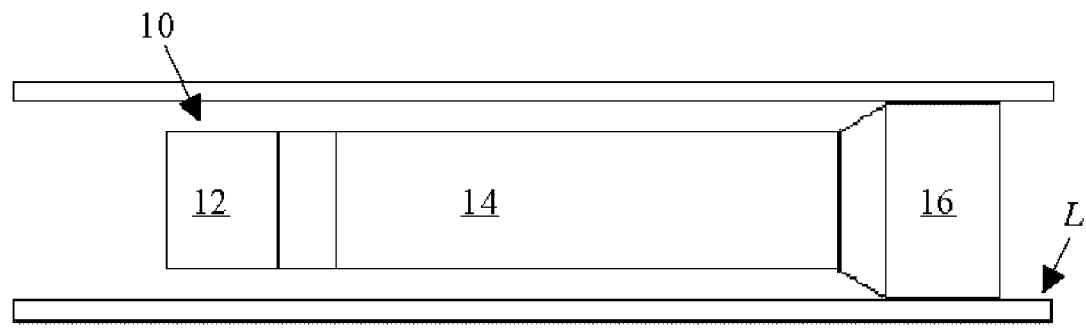
FIG. 5F is a schematic showing the lumen traversing device of FIG. 5B with the intermediate actuator electrically de-actuated to decrease a length of the device.

As previously indicated, the actuators 304, 306, 308 can be electrically actuated in a predetermined pattern that will cause the device 300 to traverse through a lumen in a tubular body part. FIGS. 5A-5F illustrate one exemplary method for traversing a lumen of a tubular body part using a device 10 that is disposed within a lumen L of a tubular body part and that has a proximal actuator 12, an intermediate actuator 14, and a distal actuator 16. As shown in FIG. 5A, the device 10 is first positioned within a lumen L with each of the actuators 12, 14, 16 being de-activated, i.e., in a resting configuration without energy being applied thereto. The proximal actuator 12 is then electrically actuated to cause the actuator 12 to expand radially and thereby engage the walls of the lumen L, as shown in FIG. 5B. With the proximal actuator 12 remaining in the actuated configuration, the intermediate actuator 14 is then electrically actuated to cause it to expand axially to thereby increase a length of the device 10 and move the distal actuator 16 in a distal direction, as shown in FIG. 5C. With the proximal and intermediate actuators 12, 14 in the actuated configuration, the distal actuator 16 is then electrically actuated to cause it to expand radially and thereby engage the walls of the lumen L, as shown in FIG. 5D. The proximal actuator 12 is then electrically de-actuated to cause the proximal actuator 12 to expand axially and contract radially to release the walls of the lumen L, as shown in FIG. 5E. Once released, the intermediate actuator 14 can be electrically de-actuated to cause it to contract axially and expand radially to decrease a length of the device 10 and to move the proximal actuator 12a distance toward the distal actuator 16, as shown in FIG. 5F. The process can be repeated to continue moving the device 10 through the lumen L until positioned as desired.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A lumen traversing medical device, comprising:
   a flexible elongate member having
   proximal and distal electroactive actuators coupled to proximal and distal portions thereof and adapted to expand radially to engage an inner wall of a lumen upon application of energy thereto, and
   a plurality of intermediate electroactive actuators coupled thereto and positioned between the proximal and distal electroactive actuators, each intermediate electroactive actuator having an elongate length with a central longitudinal axis, the central longitudinal axis of each intermediate electroactive actuator being positioned along a length of the flexible elongate member in parallel with and offset from a longitudinal axis of the flexible elongate member and being adapted to change a length of the flexible elongate member upon application of energy thereto, wherein the proximal and distal electroactive actuators retain a single shape in both an expanded configuration and a contracted configuration.

2. The device of claim 1, wherein the proximal, intermediate, and distal actuators are adapted to be actuated with energy to move the device through a lumen.

3. The device of claim 1, wherein the proximal, intermediate, and distal actuators are adapted to be sequentially actuated with energy to move the device through a lumen.

4. The device of claim 1, wherein the proximal and distal actuators are disposed around proximal and distal portions of the flexible elongate member, and the intermediate actuator is disposed between the proximal and distal actuators and extends along at least a portion of a length of the flexible elongate member.

5. The device of claim 4, wherein the intermediate actuator comprises a plurality of elongate bands extending along at least a portion of a length of the flexible elongate member.

6. The device of claim 5, wherein the plurality of elongate bands are spaced substantially equidistant from one another around a circumference of the flexible elongate member.

7. The device of claim 4, wherein the proximal, distal, and intermediate actuators each comprise a flexible conductive outer shell having an electroactive polymer and an ionic fluid disposed therein.

8. The device of claim 4, wherein each actuator comprises at least one electroactive polymer composite having at least one flexible conductive layer, an electroactive polymer layer, and an ionic gel layer.

9. The device of claim 7, wherein each of the proximal, distal, and intermediate actuators includes a delivery electrode coupled thereto and adapted to deliver energy to the actuators from an external energy source, and wherein the device further includes a return electrode coupled thereto.

10. The device of claim 1, wherein the intermediate actuator is adapted to expand axially and contract radially to increase a length of the flexible elongate member.

11. The device of claim 1, wherein the intermediate actuator is adapted to expand radially and contract axially to decrease a length of the flexible elongate member.

12. The device of claim 1, wherein the distal portion of the flexible elongate member includes an imaging mechanism disposed therein for viewing a lumen.

13. A method for traversing a lumen of a tubular body part, comprising:
positioning an elongate tubular member in a lumen of a tubular body part; and
sequentially electrically actuating various electroactive polymer portions of the elongate tubular member to cause proximal and distal electroactive polymer portions of the tubular member to expand in radius while maintaining a single shape to engage the lumen and to cause an intermediate elongate electroactive polymer portion of the tubular member to change in length while decreasing in radius to move the elongate tubular member a distance through the lumen of the tubular body part.

14. The method of claim 13, wherein the various portions of the elongate tubular member comprise a plurality of actuating members coupled to the elongate tubular member.

15. The method of claim 14, wherein the plurality of actuating members comprise at least two lumen-engaging actuating members disposed around the elongate tubular member that expand radially to engage the lumen when electrically actuated, and at least one lumen-traversing actuating member extending axially along at least a portion of a length of the elongate tubular member that change a length of the elongate tubular member to move the elongate tubular member a distance through the lumen.

16. The method of claim 15, wherein sequentially electrically actuating various portions of the elongate tubular member to move the elongate tubular member a distance through the lumen of a tubular body part comprises:
electrically actuating a first lumen-engaging actuating member to cause the first lumen-engaging actuating member to expand radially to engage the lumen;
electrically actuating a first lumen-traversing actuating member to cause the first lumen-traversing actuating member to increase a length of the elongate tubular member to move a second lumen-engaging actuating member away from the first lumen-engaging actuating member;
electrically actuating the second lumen-engaging actuating member to cause the second lumen-engaging actuating member to expand radially to engage the lumen;
electrically de-actuating the first lumen-engaging actuating member to cause the first lumen-engaging actuating member to release the lumen; and
electrically de-actuating the first lumen-traversing actuating member to cause the first lumen-traversing actuating member to decrease the length of the flexible elongate member to move the first lumen-engaging actuating member toward the second lumen-engaging actuating member.

17. The method of claim 15, wherein sequentially electrically actuating various portions of the elongate tubular member to move the elongate tubular member a distance through the lumen of a tubular body part comprises:
electrically actuating a first lumen-engaging actuating member to cause the first lumen-engaging actuating member to expand radially to engage the lumen;
electrically actuating a first lumen-traversing actuating member to cause the first lumen-traversing actuating member to decrease a length of the elongate tubular member to move a second lumen-engaging actuating member toward from the first lumen-engaging actuating member;
electrically actuating the second lumen-engaging actuating member to cause the second lumen-engaging actuating member to expand radially to engage the lumen;
electrically de-actuating the first lumen-engaging actuating member to cause the first lumen-engaging actuating member to release the lumen; and
electrically de-actuating the first lumen-traversing actuating member to cause the first lumen-traversing actuating member to increase the length of the flexible elongate member to move the first lumen-engaging actuating member away from the second lumen-engaging actuating member.

* * * * *